(12) United States Patent
Kaneda et al.

(10) Patent No.: US 9,694,041 B2
(45) Date of Patent: Jul. 4, 2017

(54) MILK YIELD AND/OR MILK QUALITY IMPROVING AGENT, PERINATAL DISEASE PREVENTIVE OR THERAPEUTIC AGENT, AND REPRODUCTIVITY IMPROVING AGENT FOR RUMINANT

(71) Applicant: IDEMITSU KOSAN CO., LTD., Chiyoda-ku (JP)

(72) Inventors: Koichi Kaneda, Tokyo (JP); Masami Mochizuki, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 0 days.

(21) Appl. No.: 14/962,591

(22) Filed: Dec. 8, 2015

(65) Prior Publication Data

US 2016/0082060 A1 Mar. 24, 2016

Related U.S. Application Data

(60) Continuation of application No. 14/314,904, filed on Jun. 25, 2014, now Pat. No. 9,238,048, which is a continuation of application No. 14/186,758, filed on Feb. 21, 2014, now Pat. No. 8,859,015, which is a division of application No. 13/978,324, filed as application No. PCT/JP2011/077694 on Nov. 30, 2011, now Pat. No. 8,697,148.

(30) Foreign Application Priority Data

Jan. 7, 2011 (JP) ................................. 2011-001711
Feb. 28, 2011 (JP) ................................. 2011-042631

(51) Int. Cl.
| | | |
|---|---|---|
| A01N 65/00 | (2009.01) | |
| A61K 36/22 | (2006.01) | |
| A61K 36/00 | (2006.01) | |
| A61K 31/05 | (2006.01) | |
| A61K 31/192 | (2006.01) | |
| A61K 31/60 | (2006.01) | |
| A61K 47/02 | (2006.01) | |
| A23K 10/37 | (2016.01) | |
| A23K 20/00 | (2016.01) | |
| A23K 20/111 | (2016.01) | |
| A23K 50/10 | (2016.01) | |

(52) U.S. Cl.
CPC ............. *A61K 36/22* (2013.01); *A23K 10/37* (2016.05); *A23K 20/00* (2016.05); *A23K 20/111* (2016.05); *A23K 50/10* (2016.05); *A61K 31/05* (2013.01); *A61K 31/192* (2013.01); *A61K 31/60* (2013.01); *A61K 36/00* (2013.01); *A61K 47/02* (2013.01); *Y02P 60/877* (2015.11)

(58) Field of Classification Search
CPC ..................................................... A61K 36/00

USPC ......................................................... 424/725
See application file for complete search history.

(56) References Cited

U.S. PATENT DOCUMENTS

| | | | |
|---|---|---|---|
| 5,725,894 | A | 3/1998 | Toyomizu et al. |
| 2009/0285931 | A1 | 11/2009 | Shelby et al. |
| 2010/0183755 | A1 | 7/2010 | Kobayashi et al. |
| 2010/0183756 | A1 | 7/2010 | Kobayashi et al. |

FOREIGN PATENT DOCUMENTS

| | | |
|---|---|---|
| CA | 2 738 819 | 4/2010 |
| CA | 2 746 574 | 6/2010 |
| EP | 2 165 609 A1 | 3/2010 |
| JP | 01-190630 A | 7/1989 |
| JP | 7-109224 A | 4/1995 |
| JP | 8-231410 A | 9/1996 |
| JP | 10-226643 A | 8/1998 |
| WO | WO 2010/053085 A1 | 5/2010 |
| WO | WO 2010/113886 A1 | 10/2010 |
| WO | WO 2010/143627 A1 | 12/2010 |

OTHER PUBLICATIONS

European Office Action issued Dec. 22, 2015 in Patent Application No. 11 855 002.9.

"Ruminal Acidosis—Understandings, Prevention and Treatment. A Review for Veterinarians and Nutritional Professionals" By the Reference Advisory Group on Fermentative Acidosis of Ruminants (RAGFAR) feed.FIBRE.future, XP055236507, Jun. 1, 2007, Retrieved from the Internet: URL:https://www.ava.com.au/sites/default/files/documents/Other/RAGFAR_doc.pdf, pp. 1-52 and Cover Pages.

(Continued)

*Primary Examiner* — Michael Meller

(74) *Attorney, Agent, or Firm* — Oblon, McClelland, Maier & Neustadt, L.L.P.

(57) ABSTRACT

An object of the present invention is to improve the milk yield and/or milk quality of a ruminant for milk production, to prevent or treat a perinatal disease of a ruminant, and to improve the reproductivity of ruminant. In order to solve the above-mentioned problem, the following is provided. An agent for improving at least one of milk yield and milk quality of a ruminant, comprising at least one of cashew nut shell liquid, heat-treated cashew nut shell liquid, anacardic acid, cardanol, and cardol. An agent for preventing or treating a perinatal disease of a ruminant, comprising at least one of cashew nut shell liquid, heat-treated cashew nut shell liquid, anacardic acid, cardanol, and cardol. An agent for improving reproductivity of a ruminant, comprising at least one of cashew nut shell liquid, heat-treated cashew nut shell liquid, anacardic acid, cardanol, and cardol.

13 Claims, 5 Drawing Sheets

(56) References Cited

OTHER PUBLICATIONS

Office Action issued on May 9, 2016 in Korean Patent Application No. 10-2013-7020623 (with unedited computer generated English language translation).
Office Action issued Dec. 28, 2016 in Chinese Patent Application No. 201410531474.9 (with English translation).
Zhou Yizai, et al., Displaced Abomasum in Cattle, *Jilin Animal Husbandry and Veterinary Medicine*, 1982, Issue 6, pp. 42-43 (with English translation).
New Zealand Office Action issued Jan. 17, 2014 in connection with corresponding New Zealand Patent Application No. 612611, filed Jun. 28, 2013.
Extended Search Report issued Jul. 24, 2014 in European Patent Application No. 11855002.9.
International Search Report issued Mar. 13, 2012 in PCT/JP2011/077694.
R. D. Goodrich et al., "Influence of Monensin on the Performance of Cattle", Journal of Animal Science, vol. 58, No. 6, 1984, pp. 1484-1498.
S. Beckett et al., "Effects of Nionensin on the Reproduction, Health, and Milk Production of Dairy Cows", Journal of Dairy Science, vol. 81, No. 6, 1998, pp. 1563-1573.
C. Benchaar et al., "Effects of Monensin and Increasing Dose Levels of a Mixture of Essential Oil Compounds on Intake, Digestion and Growth Performance of Beef Cattle", Canadian Journal of Animal Science, vol. 86, No. 1, 2006, pp. 91-96.
Hisae Muroi et al., "Synergistic Effects of Anacardic Acids and Methicillin Against Metnicillin Resistant *Staphylococcus aureus*", Bioorganic & Medicinal Chemistry, vol. 12, 2004, pp. 583-587.
C. J. Van Nevel et al., "Effect of Fatty Acid Derivatives on Rumen Methane and Propionate In Vitro", Applied Microbiology, vol. 21, No. 2, 1971, pp. 365-366.
Donna M. Arnaral-Phillips et al., "Role of Nutrition on Reproductive Performance", University of Kentucky Cooperative Extension Service, ASC-138, 1997, 4 pages.
Ricardo Mattos et al., "Effects of Dietary Fatty Acids on Reproduction in Ruminants", Reviews of Reproduction, vol. 5, 2000, pp. 38-45.
Dochi Osamu. "Current Status of Decrease in Reproductive Performance of Milk Cows and Technical Measures", Livestock Technology, vol. 649, 2009, pp. 7-12, *with English-language Translation*.

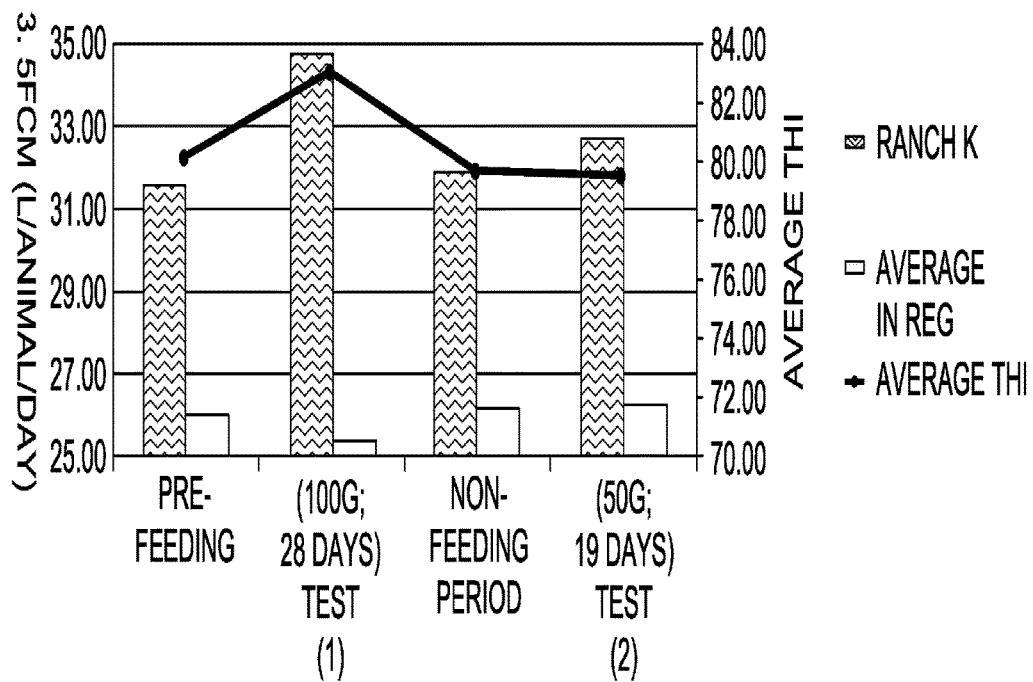

MILK YIELD AND/OR MILK QUALITY IMPROVING AGENT, PERINATAL DISEASE PREVENTIVE OR THERAPEUTIC AGENT, AND REPRODUCTIVITY IMPROVING AGENT FOR RUMINANT

CROSS-REFERENCE TO RELATED APPLICATIONS

The present application is a Continuation application of Ser. No. 14/314,904, which is a Continuation application of Ser. No. 14/186,758, now U.S. Pat. No. 8,859,015, which is a Divisional application of Ser. No. 13/978,324, now U.S. Pat. No. 8,697,148, which is a 35 U.S.C. §371 national stage application of International Patent Application PCT/JP2011/07694, filed on Nov. 30, 2011, published as WO 2012/093533 on Jul. 12, 2012, incorporated herein by reference, and claiming benefit of filing dates of Japanese Patent Application Nos. 2011-001711, filed on Jan. 7, 2011, incorporated herein by reference, and 2010-042631, filed on Feb. 28, 2011, incorporated herein by reference.

TECHNICAL FIELD

The present invention relates to an agent and a feed for improving milk yield and/or milk quality of a ruminant for milk production, and a method of improving milk yield and/or milk quail using the agent and feed. The present invention also relates to an agent and a feed for preventing or treating a perinatal disease of a ruminant, and a method of preventing or treating a perinatal disease of a ruminant using the agent and feed. Further, the present invention relates to an agent and a feed for improving a reproductivity for a ruminant, and a method of improving a reproductivity for a ruminant.

BACKGROUND ART

In the case where the ruminant is used as livestock, important factors for improving its productivity are improvement, of yield and quality of the animal product, improvement of reproductivity, and disease control. In order to address them, an antibiotic, a probiotic, an oligosaccharide, a plant extract, and the like are used. For example, an ionophore such as monensin, which is an antibiotic, has an effect of improving feed efficiency in meat production (Non Patent Document 1) and an effect of increasing milk yield in milk production (Non Patent Document 2).

However, in recent years, owing to a problem of emergence of antibiotic-resistant bacteria, addition of an antibiotic to a feed has been regulated strictly, and in Europe, the use of the antibiotic for growth promotion had been banned by January 2006. Further, there is a strong consumer's demand for safe livestock products, which are produced without using an antibiotic, and hence, a need for an alternative to the antibiotic is growing.

Therefore, uses of a plant extract and so on have been studied as technologies for the alternative to the antibiotic (Non Patent Document 3). However, many of the technologies have problems in that the effects are unstable and registration as feeds are not accepted, and have not yet been put to practical use.

It is known that cashew nut shell liquid has an antibacterial action (Non Patent Document 4) and a coccidiosis-relieving action (Patent Document 1). As for an effect of the cashew nut shell liquid on a ruminant, there is a report suggesting a methane-reducing effect in an in vitro test using anacardic acid, which is one of the components of the cashew nut shell liquid (Non Patent Document 5). Further, prevention of acidosis has been reported using ruminants (Patent Document 2). However, up to now, there have been no findings on improvement of milk productivity such as milk yield and milk quality of ruminants by the cashew nut shell liquid.

Further, a perinatal disease of cows accounts for more than half of reasons of death or disposal of milk cows and cause huge economic and mental damage on farmers. The perinatal disease is a collective term for diseases which tend to occur in a perinatal period before and after calving, such as hypocalcemia (milk fever), fatty liver, ketosis, and abomasal displacement. Of those, abomasal displacement is a disease which is characterized by displacement of the abomasum from a normal position to a left or right direction, and causes a symptom such as hypophagia. In many cases, right abomasal displacement is associated with intestinal volvulus and causes a severe symptom. In particular, this disease frequently occurs in milk cows after calving. This disease can be mainly treated only by a surgical operation and imposes a great burden on farmers because of hypodynamia of cows and an increase in medical cost.

Conventionally, abomasal displacement has been prevented or treated by the surgical operation as well as medical treatments with a probiotic (Patent Document 3), an agent containing catechins (Patent Document 4), prifinium bromide (Patent Document 5), and metoclopramide (Patent Document 5). However, these methods have stress problems to cows by intravenous or intramuscular injection, a long period for treatment (1 week or more), and a low curing rate. Further, clear preventive effects have not been shown. Hitherto, there have been no findings on prevention and treatment of perinatal diseases of ruminants by the cashew nut shell liquid.

Further, for both of beef cattle and milk cows, improvement of reproductivity is recognized as a very important problem directly linked to productivity and profitability. A period from insemination to nonlactating and calving without severe diseases is important in farmer's benefits. In the case of the milk cows, reduction of the number of artificial inseminations, reduction a feeding cost, and an increase in lifetime milk yield can be achieved by the satisfactory management of the perinatal period. In the case of the beef cattle, improvement of the number of calf and reduction of a management cost can be achieved by the smooth management of the perinatal period. They make a huge contribution to improvement of income in a farmer.

Conventionally, reproductivity has been improved not only by complete nutritional management such as securing of dry matter intake or supply of energy or proteins but also by feeding additives including vitamins such as vitamin A, vitamin D, and vitamin E, macrominerals such as calcium, phosphorus, magnesium, sodium, potassium, chlorine, and sulfur, and microminerals such as copper, cobalt, zinc, manganese, and selenium (Non Patent Document 6). Further, there is a report that addition of an unsaturated fatty acid (such as linoleic acid, eicosapentaenoic acid, or docoahexaenoic acid) can improve reproductivity (Non Patent Document 7).

However, these reports have various problems in that planned nutrients cannot be fed by hypophagia and so on, before and after calving. And the effects in these reports are unclear because individual differences of the reproductivity are large. Therefore the problems have not been solved sufficiently. Further, there are problems at a cow group level, such as increases in the number of anestrous cows, decrease of an estrus detection rate, and decrease of a conception rate, and thus the overall animal husbandry conducts repeated trials and errors (Non Patent Document 8). Further, hitherto, there have been no findings on the improvement of the reproductivity of a ruminant by the cashew nut shell liquid.

PRIOR ART DOCUMENTS

Patent Documents

Patent Document 1: JP 08-231410A
Patent Document 2: International Patent WO2010/053085A
Patent Document 3: JP 07-109224A
Patent Document 4: JP 10-226643A
Patent Document 5: JP 01-190630A Non Patent Documents Non Patent Document 1: R. D. Goodrich, et al., Journal of Animal Science, 58, 1484-1498 (1984)
Non Patent Document 2: S. BecKett, et al., Journal of Dairy Science, 81(6), 1563-1573 (1998)
Non Patent Document 3: Benchaar, et al., Can. Journal of Animal Science, 86, 91-96 (2006)
Non Patent Document 4: H. Muroi, et. al., Bioorganic & Medicinal Chemistry, 12, 583-587 (2004)
Non Patent Document 5: C. J. Van Nevel., et al., Applied Microbiology, 21, 365-366 (1971)
Non Patent Document 6: D. M. Amaral-Phillips et al., University of Kentucky Cooperative Extension Service, ASC-138 (1997)
Non Patent Document 7: R. Mattes et al., Reviews of Reproduction, 5, 38-45 (2000)
Non Patent Document 8: O. Uochi, Livestock Technology, June, 2009, 649, 7-12 (2009)

SUMMARY OF THE INVENTION

An object of the present invention is to improve the milk yield and/or milk quality of a ruminant for milk production. Another object of the present invention is to prevent or treat a perinatal disease of a ruminant. Still another object of the present invention is to improve the reproductivity of a ruminant.

The inventors of the present invention have conducted intensive studies to solve the above-mentioned problems, and as a result, the inventors have found that the administration of cashew nut shell liquid (hereinafter, sometimes abbreviated as CNSL) to a ruminant for milk production can improve the milk yield and milk quality. The inventors of the present invention have also found that the administration of cashew nut shell liquid to a ruminant can prevent or treat a perinatal disease and improve the reproductivity.

Thus, the inventors of the present invention have completed the present invention.

That is, the summary of the present invention is as follows.

(1) An agent for improving at least one of milk yield and milk quality of a ruminant, comprising at least one of cashew nut shell liquid, which may be a cashew nut shell itself, the same shall apply hereinafter, heat-treated cashew nut shell liquid, which may be a heat-treated cashew nut shell itself, the same shall apply hereinafter, anacardic acid, cardanol, and cardol.

(2) The agent for improving at least one of milk yield and milk quality according to (1), which is administered to a ruminant fed with a feed having a ratio by weight of a forage to a total weight of the forage and a concentrate feed of 0.3 to 1.0.

(3) A feed for improving at least one of milk yield and milk quality of a ruminant, comprising at least one of cashew nut shell liquid, heat-treated cashew nut shell liquid, anacardic acid, cardanol, and cardol.

(4) The feed according to (3), which has a ratio by weight forage to a total weight of the forage and a concentrate feed of 0.3 to 1.0.

(5) A method of improving at least one of milk yield and milk quality of a ruminant, comprising administering at least one of cashew nut shell liquid, heat-treated cashew nut shell liquid, anacardic acid, cardanol, and cardol to the ruminant.

(6) The method according to (5), wherein the ruminant is raised with a feed having a ratio by weight of a forage to a total weight of the forage and a concentrate feed of 0.3 to 1.0.

(7) The method according to (5) or (6), wherein at least one of cashew nut shell liquid, heat-treated cashew nut shell liquid, anacardic acid, cardanol, and cardol is administered in an amount of 0.01 to 500 g per head per day.

(8) A use of at least one of cashew nutshell liquid, heat-treated cashew nut shell liquid, anacardic acid, cardanol, and cardol for production of an agent for improving at least one of milk yield and milk quality of a ruminant.

(9) A use of at least one of cashew nut shell liquid, heat-treated cashew nut shell liquid, anacardic acid, cardanol, and cardol for production of a feed for improving at least one of milk yield and milk quality of a ruminant.

(10) An agent for preventing or treating a perinatal disease of a ruminant, comprising at least one of cashew nut shell liquid, heat-treated cashew nut shell liquid, anacardic acid, cardanol, and cardol.

(11) A feed for preventing or treating a perinatal disease a ruminant, comprising at least one of cashew nut shell liquid, heat-treated cashew nut shell liquid, anacardic acid, cardanol, and cardol.

(12) A method of preventing or treating a perinatal disease of a ruminant, comprising administering at least one of cashew nut shell liquid, heat-treated cashew nut shell liquid, anacardic acid, cardanol, and cardol to the ruminant.

(13) A use of at least one of cashew nut shell liquid, heat-treated cashew nut shell liquid, anacardic acid, cardanol, and cardol for production of an agent for preventing or treating a perinatal disease of a ruminant.

(14) A use of at least one of cashew nut shell liquid, heat-treated cashew nut shell liquid, anacardic acid, cardanol, and cardol for production of a feed for preventing or treating a perinatal disease of a ruminant.

(15) An agent for improving reproductivity of a ruminant, comprising at least one of cashew nut shell liquid, heat-treated cashew nut shell liquid, anacardic acid, cardanol, and cardol.

(16) A feed for improving reproductivity of a ruminant, comprising at least one of cashew nut shell liquid, heat-treated cashew nut shell liquid, anacardic acid, cardanol, and cardol.

(17) A method of improving reproductivity of a ruminant, comprising feeding at least one of cashew nut shell liquid, heat-treated cashew nut shell liquid, anacardic acid, cardanol, and cardol to the ruminant.

(18) The method according to (17), wherein at least one of cashew nut shell liquid, heat-treated cashew nut shell liquid, anacardic acid, cardanol, and cardol is fed in an amount of 0.01 to 500 g per head per day.

(19) A use of at least one of cashew nut shell liquid, heat-treated cashew nut shell liquid, anacardic acid, cardanol, and cardol for production of an agent for improving reproductivity of a ruminant.

(20) A use of at least one of cashew nut shell liquid, heat-treated cashew nut shell liquid, anacardic acid, cardanol, and cardol for production of a feed for improving reproductivity of a ruminant.

The administration of the agent or feed containing cashew nut shell liquid, heat-treated cashew nut shell liquid, anacardic acid, cardanol, and/or cardol of the present invention to a ruminant for milk pr duct ion can improve the milk yield and/or milk quality (e.g., milk protein content, solids-not-fat content, and milk fat content). Further, the feeding of the agent or feed in the course of an increase in the milk yield after calving can improve the rate of an increase in the milk yield.

Although milk may not receive a high evaluation when the solids-not-fat content and milk fat content are lower than standard values, the agent for improving milk quality of the present invention can prevent a decrease in a milk price (purchase price from a farmer).

The agent for improving milk quality of the present invention can provide milk with higher milk component levels such as a milk protein content, a solids-not-fat content, and a milk fat content than standard values. Therefore, in the case where a milk price depends on an evaluation of milk quality, the milk price may be raised to give larger profits to a farmer.

The administration of the agent or feed containing cashew nut shell, liquid, heat-treated cashew nut shell liquid, anacardic acid, cardanol, and/or cardol of the present invention to a ruminant can prevent or treat a perinatal disease such as abomasal displacement. Thus, death or disposal of a ruminant before or after calving can be prevented.

The feeding of the agent or feed containing cashew nut shell liquid, heat-treated cashew nut shell liquid, anacardic acid, cardanol, and/or cardol of the present invention to a ruminant can lead to the improvement of the reproductivity such as a reduction in the number of insemination and a decrease in days of non-pregnant. Thus, the feeding can efficiently provide offspring and can increase the amount of milk produced in its life, resulting in significantly improving the productivity.

As mentioned above, the administration of the agent or feed containing cashew nut shell liquid, heat-treated cashew nut shell liquid, anacardic acid, cardinal, and/or cardol of the present invention to a ruminant for milk production can prevent or treat a perinatal disease after calving and can increase the milk yield. Therefore, the agent or feed is very useful for raising a ruminant such as a milk cow. It should be noted that although the incidence of the perinatal disease decreases over time after calving, the agent or feed can increase the milk yield and improve the milk quality even after that time. Further, the improvement of the reproductivity can efficiently provide offspring, reduce a cost for artificial insemination, and reduce a cost for a feeding system, and hence the agent or feed enables long-term rebreeding or improvement of the productivity.

MODES FOR CARRYING OUT THE INVENTION

Figure 1:
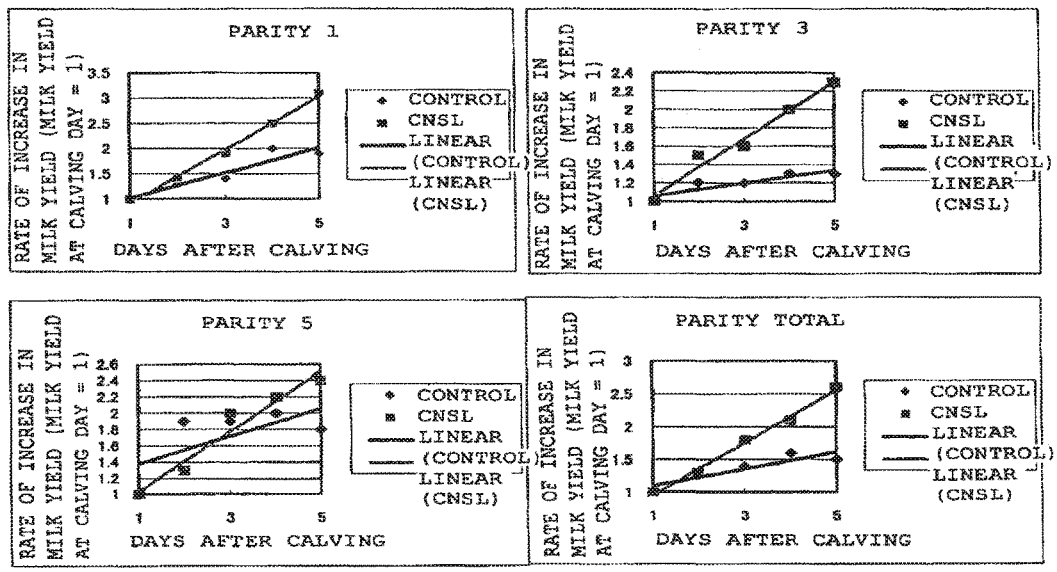
FIG. 1 is a graph showing relationships between days after calving and a rate of increase in milk yield in CNSL-fed group and control group.

An agent for improving milk yield and/or milk quality of a ruminant of the present invention contains cashew nut shell liquid (CNSL), heat-treated cashew nut shell liquid, anacardic acid, cardanol, and/or cardol. It should be noted that, in the present invention, the milk yield refers to an amount of milk obtained by a single milking, and the improvement of milk yield includes amelioration and increase of the milk yield. In the present invent ion, the milk quality includes indices such as a milk protein content, a solids-not-fat content, and a milk fat content, and the milk protein content, solids-not-fat content, and milk fat content are preferably higher. In the present invention, the improvement of milk quality includes the amelioration and increase of the milk quality and particularly refers to the amelioration and increase C) the milk protein content, solids-not-fat content, and milk fat content.

An agent for preventing or treating a perinatal disease of a ruminant of the present invention contains cashew nut shell liquid (CNSL), heat-treated cashew nut shell liquid, anacardic acid, cardanol, and/or cardol. It should be noted that, in the present invention, the perinatal disease refers to a disease which develops in a ruminant after calving. Specific examples thereof include hypocalcemia (milk fever), fatty liver, ketosis, and abomasal displacement.

An agent for improving a reproductivity of the present invention contains cashew nut shell liquid (CNSL), heat-treated cashew nut shell liquid, anacardic acid, cardanol, and/or cardol. It should be noted that, in the present invention, the improvement of a reproductivity refers to efficiently producing offspring due to the decrease of a number of insemination, the decrease of days of non-pregnant, the improvement of a pregnancy rate, and the reduction of actual days of non-pregnant.

The cashew nut shell liquid is an oily liquid contained in the shell of the seed of a cashew nut tree (*Anacardium occidentale* L.). The cashew nut shell liquid contains, as components thereof, anacardic acid, cardanol, and cardol. In general, anacardic acid is converted into cardanol by a heat-treatment. Thus, heat-treated cashew nut shell liquid containing cardanol and cardol only may be used.

Non-heated cashew nut shell liquid extracted by compressing the shell of a cashew nut contains 55 to 80 mass % anacardic acid, 5 to 20 mass % cardanol, and 5 to 30 mass % cardol as described in J. Agric. Food Chem. 2001, 49, 2548-2551.

Heated cashew nut shell liquid obtained by heat-treating non-heated cashew nut shell liquid at 130° C. or higher contains 0 to 10 mass % anacardic acid, 55 to 80 mass % cardanol, and 5 to 30 mass % cardol, because anacardic acid which is a major component of non-heated cashew nut shell liquid is converted into cardanol by decarboxylation.

The cashew nut shell liquid used in the present invention can be obtained as a vegetable oil extracted by compressing the shell of a cashew nut. Further, the cashew nut shell liquid used in the present invention can also be obtained by heating or extracting, e.g., dry distillation or solvent-extraction of cashew nut shells. In addition, the cashew nut shell liquid used in the present invention can be obtained according to a method described in JP 08-231410 A.

The cashew nut shell liquid used in the present invention may also be heat sterilized oil or a liquid obtained by pulverizing/crushing the shell of a cashew nut. Further, the shell itself may be used.

For the cashew nut shell liquid used in the present invention, a commercially-available product may also be used.

The heated cashew nut shell liquid of the present invention can be obtained by heating cashew nut shell liquid obtained as above to 70° C. or higher, preferably 130° C. or higher. Note that when heat-treated cashew nut shell liquid is used, the mass ratio of anacardic acid to cardanol in the heated cashew nut shell liquid is preferably 0:100 to 20:80.

The milk yield and/or milk quality improving agent, the perinatal disease preventive or therapeutic agent, and the reproductivity improving agent of the present invention can contain anacardic acid, cardanol, and/or cardol instead of a cashew nut shell liquid.

As anacardic acid used in the present invention, there are exemplified natural anacardic acid, synthetic anacardic acid, and the derivatives thereof. Further, commercially-available anacardic acid may be used. As described in JP 08-231410 A, anacardic acid may be obtained, for example, by eluting the cashew nut shell liquid, which has been obtained by subjecting the cashew nut shell to extraction treatment with an organic solvent, through chromatography on a silica gel column using a solvent of n-hexane, ethyl acetate, and acetic acid mixed at varied ratios (JP 03-2407 A, JP 03-240716 A, and the like).

Examples of the cardanol used in the present invention include natural cardanol, synthetic cardanol, and derivatives thereof. The cardanol used in the present invention can be obtained by decarboxylation of anacardic acid which is a major component of cashew nut shell liquid.

Examples of the cardol used in the present invention include natural cardol, synthetic cardol, and derivatives thereof. The cardol used in the present invention can be purified from cashew nut shell liquid.

The content of the cashew nut shell liquid, the heat-treated cashew nut shell liquid, anacardic acid, cardanol, and/or cardol in the milk yield and/or milk quality improving agent, the perinatal disease preventive or therapeutic agent, and the reproductivity improving agent of the present invention is, on the basis of the total amount, preferably 0.1 to 100 mass %, more preferably 0.5 to 95 mass %, and particularly preferably 1 to 90 mass %. When the content is 0.1 ma or more, it can be expected that milk yield and/or milk quality are improved, a perinatal disease is prevented or treated, and reproductivity is improved. The tendency is remarkable when the content is 0.5 mass % or more and particularly preferably 1 mass % or more, which is preferred. On the other hand, although milk yield and/or milk quality are improved, a perinatal disease is prevented or treated, and reproductivity is improved even when the content is 100 mass %, the content is preferably 95 mass % or less and particularly preferably 90 mass % or less.

In the present invention, a stock solution of the cashew nut shell liquid, the heat-treated cashew nut shell liquid, anacardic acid, cardanol, and/or cardol may be directly orally administered.

In the case where the stock solution of the cashew nut shell liquid, the heat-treated cashew nut shell liquid, anacardic acid, cardanol, and/or cardol of the present invention is directly administered, the dose of the cashew nut shell liquid, the heat-treated cashew nut shell liquid, anacardic acid, cardanol, and/or cardol is preferably 0.01 to 500 g per ruminant per day, more preferably 0.1 to 200 g per ruminant per day, and most preferably 1 to 100 g per ruminant per day. When the content is 0.01 g per ruminant per day or more, it can be expected that milk yield and/or milk quality are improved, a perinatal disease is prevented or treated, and reproductivity is improved. The tendency is remarkable when the content is 0.1 g or more and particularly preferably 1 g or more, which is preferred. On the other hand, although milk yield and/or milk quality are improved, a perinatal disease is prevented or treated, and reproductivity is improved even when the content is 1000 g or less, the content is preferably 200 g or less and particularly preferably 100 g or less.

The milk yield and/or milk quality improving agent, the perinatal disease preventive or therapeutic agent, and the reproductivity improving agent of the present invention may contain, in addition to a cashew nut shell liquid, a heat-treated cashew nut shell liquid, anacardic acid, cardanol, and/or cardol, any carrier as long as the carrier can be used for a feed, a drug, or a food product, such as lactose, saccharose, D-mannitol, α starch, starch, corn starch, crystalline cellulose, bentonite, silica gel, and light anhydrous silicic acid.

The milk yield and/or milk quality improving agent, the perinatal disease preventive or therapeutic agent, and the reproductivity improving agent of the present invention may further contain, in addition to a cashew nut shell liquid, a heat-treated cashew nut shell liquid, anacardic acid, cardanol, and/or cardol, an arbitrary component (s) such as a component which is effective for the growth promotion of the ruminant, a nutritional supplement component, a component for enhancing the preservation stability, or a coating component. Examples of the arbitrary components include raw materials for a feed and a feed additive such as wheat bran, alfalfa, and timothy hay, raw materials for a food and a food additive, raw materials for a medicine, and other supplement components used for animal supplements (hereinafter referred to as supplement) For example, the followings are included: probiotics such as *Enterococcus* spp., *Bacillus* spp., and *Bifidobacterium* spp.; enzymes such as amylase and lipase; vitamins such as L-ascorbic acid, choline chloride, inositol, and folate; minerals such as potassium chloride, iron citrate, magnesium oxide, and phosphates; amino acids such as DL-alanine, DL-methionine, L-lysine; organic acids such as fumaric acid, butyric acid, lactic acid, acetic acid, and their salts; antioxidants such as ethoxyquin, dibutylhydroxytoluene, butylhydroxyanisol, ferulic acid, vitamin C, and vitamin E; fungicides such as calcium propionate; binders such as carboxylmethyl cellurose (CMC), casein sodium, and sodium polyacrylate; emulsifiers such as lecithin, glycerin fatty acid ester and sorbitan fatty acid ester; pigments such as astaxanthin and canthaxanthin; and flavoring agents such as various esters, ethers, and ketones. Types of the supplement and components other than a cashew nut shell liquid, a heat-treated cashew nut shell liquid, anacardic acid, cardanol, and/or cardol are not particularly limited.

The milk yield and/or milk quality improving agent, the perinatal disease preventive or therapeutic agent, and the reproductivity improving agent of the present invention may contain magnesium oxide, stearate, talc, zeolite, diatom earth, and silica as an oil absorbent. The oil absorbent is preferably particulate. The oil adsorbent of the present invention preferably adsorbs an oil in an amount of 50 to 300 g per 100 g of the adsorbent. In addition, the particle size of the adsorbent is preferably 2 to 300 µm because particles become coarse to cause separation when the particle size exceeds 300 µm.

In the milk yield and/or milk quality improving agent, the perinatal disease preventive or therapeutic agent, and the reproductivity improving agent of the present invention, the mass ratio of the oil absorbent and a cashew nut shell liquid (CNSL), a heat-treated cashew nut shell liquid, anacardic acid, cardanol, and/or cardol is preferably 100:20 to 100:180. Further, the mass ratio of the oil absorbent and the pulverized products of a cashew nut shell is preferably 15:100 to 60:100.

The dosage form of the milk yield and/or milk quality improving agent, the perinatal disease preventive or therapeutic agent, and the reproductivity improving agent of the present invention is not particularly limited, and the agent may be in an arbitrary form such as a liquid formulation, a powder formulation, a solid, a tablet, a capsule, an emulsion, a pellet, a tablet, and a coated formulation, and preferred are a liquid formulation, a powder formulation, a capsule, a pellet, and a tablet.

As the liquid formulation, the cashew nut shell liquid, the heat-treated cashew nut shell liquid, anacardic acid, cardanol, and/or cardol may be used as it is, the cashew nut shell liquid, the heat-treated cashew nut shell liquid, anacardic acid, cardanol, and/or cardol may be dissolved in a solvent such as ethanol, or the cashew nut shell liquid, the heat-treated cashew nut shell liquid, anacardic acid, cardanol, and/or cardol may be used after the carrier or an arbitrary component is added. Further, the following powder, capsule, pellet, and tablet formulation may be suspended and/or floated into a liquid.

The powder formulation may be obtained by adding the carrier to the cashew nut shell liquid, the heat-treated cashew nut shell liquid, anacardic acid, cardanol, and/or cardol and forming the mixture into powder.

The capsule may be obtained by filling the cashew nut shell liquid, the heat-treated cashew nut shell liquid, anacardic acid, cardanol, and/or cardol into a capsule as it is, or by adding the carrier or an arbitrary component thereto.

The pellet may be obtained by adding the carrier to the cashew nut shell liquid, the heat-treated cashew nut shell liquid, anacardic acid, cardanol, and/or cardol, and granulating and pelletizing the mixture.

The tablet formulation may be obtained by adding the carrier to the cashew nut shell liquid, the heat-treated cashew nut shell liquid, anacardic acid, cardanol, and/or cardol, granulating the mixture, and tableting the resultant.

Note that in the case when an oil absorbent such as silica is used, a powder, tablet, or pellet formulation is preferred.

As described above, the milk yield and/or milk quality improving agent, the perinatal disease preventive or therapeutic agent, and the reproductivity improving agent of the present invention can be produced by mixing the cash nut shell liquid, the heat-treated cashew nut shell liquid, anacardic acid, cardanol, and/or cardol with, if necessary, a carrier or an arbitrary component and formulating the mixture. Note that, depending on the form of the formulation, the above-mentioned pulverized/crushed product of the cashew nut shell or the cashew nut shell as it is without being subjected to any treatment is mixed with another arbitrary component (a), and the mixture can be used as the milk yield and/or milk quality improving agent, the perinatal disease preventive or therapeutic agent, and the reproductivity improving agent of the present invention. In addition, without being mixed with another arbitrary component (s), the pulverized/crushed product as it is or the cashew nut shell as it is may be used as the milk yield and/or milk quality improving agent, the perinatal disease preventive or therapeutic agent, and the reproductivity improving agent of the present invention, and the milk yield and/or milk quality improving agent, the perinatal disease preventive or therapeutic agent, and the reproductivity improving agent of the present invention as it is may also be used as a feed. Further, the cashew nut shell liquid, the heat-treated cashew nut shell liquid, anacardic acid, cardanol, and/or cardol are dissolved in a solvent such as ethanol and the resultant can be mixed and absorbed to a feed.

Thus, the milk yield and/or milk quality improving agent, the perinatal disease preventive or therapeutic agent, and the reproductivity improving agent of the present invention comprise an effective amount of cashew nut shell liquid, heat-treated cashew nut shell liquid, anacardic acid, cardanol, and/or cardol.

The feed additive of the present invention comprises a cashew nut shell liquid, a heat-treated cashew nut shell liquid, anacardic acid, cardanol, and/or cardol.

The content of the cashew nut shell liquid, the heat-treated cashew nut shell liquid, anacardic acid, cardanol, and/or cardol in the feed additive of the present invention is, based on the dry matter mass of a feed to which the feed additive is added, on the basis of the total amount, preferably 5 to 500,000 mass ppm, more preferably 50 to 300,000 mass ppm, and particularly preferably 500 to 100,000 mass ppm. When the content is 5 mass ppm or more, it can be expected that milk yield and/or milk quality are improved, a perinatal disease is prevented or treated, and reproductivity is improved. The tendency is remarkable when the content is 50 mass ppm or more and particularly preferably 500 mass ppm or more, which is preferred. On the other hand, although milk yield and/or milk quality are improved, a perinatal disease is prevented or treated, and reproductivity is improved even when the content is 500,000 mass ppm, the content is preferably 300,000 mass ppm or less and particularly preferably 100,000 mass ppm or less.

The kind of an animal to be fed with the feed additive of the present invention is a ruminant for milk production and for reproduction. For example, the feed additive of the present invention is suitable for raising ruminants such as cattle, buffaloes, goats, sheep, and yaks. As preferred species of the cattle, there are given female Holstein, Jersey, Japanese black, Japanese Shorthorn, and Aberdeen Angus. The amount of the feed ingested by an animal may be appropriately adjusted depending on the kind, body weight, age, sex, and health condition of the animal, feed components, and the like.

In this case, an amount of the feed additive to be used is, as the amount of the cashew nut shell liquid, the heat-treated cashew nut shell liquid, anacardic acid, cardanol, and/or cardol, preferably 0.1 to 500 g per head per day, more preferably 1 to 200 g per head per day, still more preferably 10 to 100 g per head per day. Further, the body weight of cattle to be fed with the feed usually ranges from 500 to 900 kg, and hence the amount of cashew nut shell liquid etc. contained in a feed fed per day per kg of the body weight of the cow is 0.00011 g to 1 g, preferably 0.0011 g to 0.4 g, more preferably 0.001 g to 0.2 g.

The feed of the present invention comprises a cashew nut shell liquid, a heat-treated cashew nut shell liquid, anacardic acid, cardanol, and/or cardol.

The content of the cashew nut shell liquid, the heat-treated cashew nut shell liquid, anacardic acid, cardanol, and/or cardol in the feed of the present invention is, based on the dry matter mass of the feed, on the basis of the total amount, preferably 0.5 to 500,000 mass ppm, more preferably 5 to 300,000 mass ppm, and particularly preferably 50 to 100,000 mass ppm. When the content is 0.5 mass ppm or more, it can be expected that milk yield and/or milk quality are improved, a perinatal disease is prevented or treated, and reproductivity is improved. The tendency is remarkable when the content is 5 mass ppm or more and particularly preferably 50 mass ppm or more, which is preferred. On the other hand, although milk yield and/or milk quality are improved, a perinatal disease is prevented or treated, and reproductivity, is improved even when the content is 500,000 mass ppm, the content is preferably 300,000 mass ppm or less and particularly preferably 100,000 mass ppm or less.

In the feed of the present invention, the kind and blending ratio of the feed component to be blended with the agent of the present invention are not particularly limited. The feed may be one conventionally given to animals. For example, the feed may be prepared using corn kernel, corn powder, milo, wheat bran, soybean meal, oat, wheat flour short, wheat coarse flour, alfalfa, timothy, clover, defatted rice bran, white fish meal, fish meal, yeast, molasses, meat pieces, born meal, calcium carbonate, dibasic calcium phosphate, yellow grease, vitamins, or minerals.

The feed of the present invention can be produced by adding cashew nut shell liquid, heat-treated cashew nut shell liquid, anacardic acid, cardanol, and/or cardol as it is, or the agent for improving milk yield and/or milk quality, agent for preventing or treating a perinatal disease, or agent for improving reproductivity of the present invention, containing cashew nut shell liquid, heat-treated cashew nut shell liquid, anacardic acid, cardanol, and/or cardol to a feed component and mixing the resultant. At this time, when a powdery or solid agent is used, the agent may be formed into a liquid form or a gel form using a liquid carrier for the purpose of facilitating the mixing process. In this case, as the liquid carrier, there may be used a flowing liquid such as water, a vegetable oil, a liquid animal oil, a mineral oil, a synthetic oil, or a water-soluble polymer compound. Further, in order to keep the homogeneity of the cashew nut shell liquid, heat-treated cashew nut shell liquid, anacardic acid, cardanol, and/or cardol in the feed, the feed preferably contains alginic acid, sodium alginate, xanthan gum, carboxymethyl cellulose, α starch, sodium caseinate, gum arabic, guar gum, or a water-soluble polysaccharide such as tamarind seed polysaccharide.

The kind of an animal to be fed with the feed of the present invention is a ruminant for milk production and for reproduction. For example, the feed of the present invention is suitable for raising ruminants such as cattle, buffaloes, goats, sheep, and yaks. As preferred species of the cattle, there are given female Holstein, Jersey, Japanese black, Japanese Shorthorn, and Aberdeen Angus. The amount of the feed ingested by an animal may be appropriately adjusted depending on the kind, body weight, age, sex, and health condition of the animal, feed components, and the like. In this case, the amount of cashew nut shell liquid etc. contained in the feed is preferably 0.01 to 500 g per head per day, more preferably 0.1 to 200 g per head per day, still more preferably 1 to 100 g per head per day. Further, the body weight of cattle to be fad with the feed usually ranges from 500 to 900 kg, and hence the amount of cashew nut shell liquid etc. contained in a feed fed per day per kg of the body weight of the cow is 0.000011 g to 1 g, preferably 0.00011 g to 0.4 g, more preferably 0.0011 q to 0.2 g.

In the feed of the present invention, the forage/concentrate ratio (ratio by weight of a forage to a concentrate feed), i.e., the ratio by weight of the forage to the total weight of the forage and concentrate feed (forage/forage+concentrate feed) is preferably between 0.3 and 1.0, more preferably between 0.3 and 0.9, still more preferably between 0.3 and 0.8.

It should be noted that the forage refers to fresh forage, silage, hay, straw, and so on out of feeds to be fed to livestock. The forage is essential for ruminant livestock to maintain the function of the ruminant stomach and serves as a major energy or nutrient supply source.

In addition, the concentrate feed is a protein- and fatty ingredient-rich feed and is produced mainly from a seed part grain such as corn, barley, wheat, or rice, legumes such as soybeans, or oil cake obtained after oil pressing.

The feed for improving milk yield and/or milk quality of the present invention is preferably fed to a milk cow aged some months suitable for milk production (usually 20 to 144 months old, preferably 20 to 132 months old, more preferably 20 to 108 months old) The agent for preventing or treating a perinatal disease is preferably fed to a periparturient cow (preferably 60 days before calving to 30 days after calving, more preferably 30 days before calving to 30 days after calving). The agent for improving reproductivity is preferably fed to a cow aged some months suitable for reproduction (usually 14 to 144 months old, preferably 14 to 132 months old, more preferably 14 to 108 months old).

It should be noted that the administration of cashew nut shell liquid, heat-treated cashew nut shell liquid, anacardic acid, cardanol, and/or cardol to a ruminant fed with a feed having a ratio by weight of a forage to the total weight of the forage and a concentrate feed of 0.3 to 1.0 (preferably 0.3 to 0.8, more preferably 0.3 to 0.7) for 2 days or more, preferably 3 days or more, more preferably 9 days or more can achieve an effect of improving the milk yield and/or milk quality, an effect of preventing or treating the perinatal disease, and an effect of improving the reproductivity.

EXAMPLES

Production Example 1

220 kg of cashew nut shells were obtained from Cashew Trading Co., Ltd., and the shells were compressed, thereby producing 67 kg of cashew nut shell liquid. In addition, heat-treated cashew nut shell, liquid obtained by conducting a heat treatment at 130° C. to convert anacardic acid into cardanol was obtained from Cashew Trading Co., Ltd. (cold-pressed oil (made in India)).

The compositions of the cashew nut shell liquids were measured by the following method. That is, HPLC (Waters 600, Nihon Waters a detector (Waters 490E, Nihon Waters K.K.), a printer (Chromatopak C-R6A, Shimadzu Corporation), and a column (SUPELCOSIL LC16, SUPELCO, Inc.) were used. A solvent of acetonitrile:water:acetic acid-60: 20:1 (volume ratio) was used and a flow rate was 2 ml/min. Detection was performed based on an absorbance at 280 nm.

The cashew nut shell liquid was found to contain 61.8 mass % of anacardic acid, 8.2 mass % of cardanol, and 19.9 mass % of cardol. The heat-treated cashew nut shell liquid was found to contain 0.0 mass % of anacardic acid, 71.4 mass % of cardanol, and 14.4 mass % of cardol.

1,000 g of silicic anhydride manufactured by Evonik Degussa Japan, Sipernat 22) was mixed with 1,000 g of cashew nut shell liquid to prepare cashew nut shell liquid-containing silica. 1,330 g of rice bran, 1,165 g of wheat flour, 1,000 g of alfalfa meal, 500 g of a molasses-containing feed, and 5 g of a flavoring agent were mixed with 1,000 g of cashew nut shell liquid-containing silica, and the mixture was pelletized to prepare a cashew nut shell liquid-containing pellet (agent for improving milk yield and/or milk quality) (oil content relative to the whole agent: 10%).

Example 1: Evaluation of Effect of Improving Milk Yield and Milk Quality

This test was conducted in a ranch where the average number of milk cows was 38 per day, and adult female Holstein cows (average: 57.5 months old, range: 25 months old to 90 months old) were used in the test. A feed to be fed (forage/concentrate ratio in the feed=1:2) was designed so that 3 kg of alfalfa, 3 kg of timothy, 8 kg of a mixed feed for milk cow breeding (manufactured by Kyodo Shiryo Co., Ltd.), and 4 kg of a mixed feed for milk cow breeding (manufactured by Snow Brand Seed Co., Ltd.) were ingested per day.

Before the feeding of the cashew nut shell liquid-containing pellet, the milk yield and milk components (milk fat content, solids-not-fat content, milk protein content, and milk urea nitrogen) were measured. The milk yield was calculated by dividing the amount of the whole milk gathered at the test ranch by the number of milk cows, and the milk component levels were analyzed for a sample obtained from the whole milk. The feeding of the cashew nut shell liquid-containing pellet was started in an amount of 100 g per day (10 g per day in terms of cashew nut shell liquid) per head, and the measurement of the milk yield and analysis of the milk quality were conducted before the start of the feeding and on Day 9 after the start of the feeding.

The milk fat content, solids-not-fat content, and milk protein content were measured in accordance with a measurement method described in:

"Ministerial Ordinance Concerning Compositional Standards, etc. for Milk and Milk Products"

(MHW Ordinance No. 52 dated Dec. 27, 1951)

Final revision: MHLW Ordinance No. 132 dated Oct. 30, 2007) Appendix

2. Compositional standards for milk etc., and standards of production, cooking, and preservation methods (7) Test method for compositional standards for milk etc. Table 1 shows the test results.

TABLE 1

|  | Before feeding of CNSL-containing pellet | Day 9 after feeding of CNSL-containing pellet | Increase or decrease amount |
|---|---|---|---|
| Milk yield (L/head) | 22.9 | 24.6 | +1.7 |
| Milk fat content (%) | 3.70 | 3.80 | +0.10 |
| Solids-not-fat content (%) | 8.85 | 8.96 | +0.11 |
| Milk protein content (%) | 3.36 | 3.50 | +0.14 |
| Milk urea nitrogen (mg/dL) | 13.4 | 11.2 | −2.2 |

The feeding of the cashew nut shell liquid-containing pellet increased the milk yield by 1.7 L on Day 9, and the pellet was found to have an effect of improving the milk yield. Further, the milk fat content, solids-not-fat content, and milk protein content increased by 0.10%, 0.11%, and 0.14%, respectively, and the pellet was found to have an effect of improving the milk quality. In addition, the milk urea nitrogen was found to decrease. This is probably because the milk protein content increased through efficient conversion of nitrogen into a milk protein.

Example 2: Evaluation of Effect of Improving Milk Yield

Adult female Holstein cattle were used in this test. The agent of Production Example 1 was fed in an amount of 100 g (10 g in terms of CNSL) per day for 5 days from the date of calving. 11 cows (one calving: 5 cows, two calvings: 1 cow, three calvings: 4 cows, five calvings: 1 cow) were allocated to CNSL-fed group, while 12 cows (one calving: 5 cows, three calvings: 4 cows, four calvings: 1 cow, five calvings: 2 cows) were allocated to control group fed with no CNSL (CNSL-unfed group). Although the feed to be fed was modified depending on the condition of the cows, the feed was designed so that 7 kg of timothy and 2 to 3 kg of a concentrate feed were fed on average per day. The milk yields were measured for 5 days from the date of calving, and the rates of increase were calculated. FIG. 1 and Tables 2 and 3 show the results.

TABLE 2

Changes of milk yield in control group (CNSL is not fed)

| Number of days after calving | Milk yield (kg/day) | | | | | | | | | | | |
|---|---|---|---|---|---|---|---|---|---|---|---|---|
| | Individual 1 | Individual 2 | Individual 3 | Individual 4 | Individual 5 | Individual 6 | Individual 7 | Individual 8 | Individual 9 | Individual 10 | Individual 11 | Individual 12 |
| 1 | 1.0 | 1.0 | 1.0 | 1.0 | 1.0 | 1.0 | 1.0 | 1.0 | 1.0 | 1.0 | 1.0 | 1.0 |
| 2 | 1.1 | 1.1 | 1.2 | 0.8 | 1.8 | 1.3 | 1.9 | 1.3 | 1.2 | 1.2 | 1.0 | 1.7 |
| 3 | 1.0 | 1.0 | 1.2 | 1.0 | 1.8 | 1.5 | 1.9 | 1.6 | 1.1 | 1.1 | 1.2 | 1.6 |
| 4 | 1.1 | 1.1 | 1.2 | 1.0 | 1.9 | 1.8 | 2.0 | 2.2 | | | 1.6 | 1.7 |
| 5 | 1.0 | 1.1 | 1.2 | 0.9 | 1.8 | 2.0 | 1.7 | 1.9 | | | | |
| 6 | 1.0 | | 1.3 | 0.9 | 2.0 | 2.9 | 2.6 | | | | | |
| 7 | | | | 1 | | | | | | | | |
| Parity | 3 | 3 | 3 | 4 | 5 | 3 | 5 | 1 | 1 | 1 | 1 | 1 |

TABLE 3

Changes of milk yield in CNSL feeding group

| Number of days after calving | Milk yield (kg/day) | | | | | | | | | | |
|---|---|---|---|---|---|---|---|---|---|---|---|
| | Individual 1 | Individual 2 | Individual 3 | Individual 4 | Individual 5 | Individual 6 | Individual 7 | Individual 8 | Individual 9 | Individual 10 | Individual 11 |
| 1 | 1.0 | 1.0 | | 1.0 | 1.0 | 1.0 | 1.0 | 1.0 | 1.0 | 1.0 | 1.0 |
| 2 | 1.3 | 1.1 | 1.0 | 1.2 | 0.9 | 1.1 | 1.2 | 2.5 | 1.1 | 1.6 | 0.7 |
| 3 | 2.0 | 1.8 | 2.5 | 1.0 | 1.5 | 1.1 | 1.2 | 2.8 | 1.3 | 1.4 | 2.7 |

TABLE 3-continued

Changes of milk yield in CNSL feeding group

| Number of days after calving | Milk yield (kg/day) | | | | | | | | | | |
|---|---|---|---|---|---|---|---|---|---|---|---|
| | Individual 1 | Individual 2 | Individual 3 | Individual 4 | Individual 5 | Individual 6 | Individual 7 | Individual 8 | Individual 9 | Individual 10 | Individual 11 |
| 4 | 2.2 | 1.7 | 2.6 | 1.1 | 1.6 | 1.2 | 1.4 | 4.2 | 1.5 | 1.6 | 3.8 |
| 5 | 2.4 | 1.8 | 4.1 | 1.1 | | 1.2 | 1.8 | 4.8 | 1.4 | | 4.4 |
| 6 | | | 5.2 | | | 1.3 | 1.9 | 4.5 | 1.8 | | 5.6 |
| Parity | 5 | 3 | 3 | 3 | 2 | 3 | 1 | 1 | 1 | 1 | 1 |

In all the parities, the feeding of CNSL increased the rates of increase in the milk yield compared with control group. The feeding of CNSL was found to increase the milk yield after calving.

Example 3: Evaluation of Effect of Preventing Abomasal Displacement

Adult female Holstein cattle were used in this test. The agent of Production Example 1 was fed in an amount of 100 g (10 g in terms of CNSL) per day for 5 days from the date of calving. 16 cows were allocated to CNSL-fed group, while 15 cows were allocated to control group fed with no CNSL. Although the feed to be fed was modified depending on the condition of the cows, the feed was designed so that 7 kg of timothy and 2 to 3 kg of a concentrate feed were fed on average per day roughly.

Figure 2:
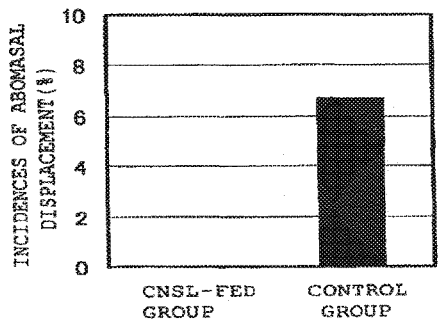
FIG. 2 is a graph showing incidences of abomasal displacement in CNSL-fed group and control group.

The onset and cure of abomasal displacement were evaluated based on findings by a veterinarian. FIG. 2 shows the test results. In CNSL-fed group, there were no cows which developed abomasal displacement, but in control group, 6.7% of the cows developed abomasal displacement. The feeding of CNSL was found to provide an effect of preventing abomasal displacement.

Production Example 2

220 kg of cashew nut shells were obtained from Cashew Trading Co., Ltd., and the shells were compressed, thereby producing 67 kg of cashew nut shell liquid. 394 g of silicic anhydride (manufactured by Evonik Degussa Japan, Sipernat 22) and 91 g of bentonite were mixed with 455 g of the cashew nut shell thereby preparing cashew nut shell liquid-containing silica. Then, a tablet of the cashew nut shell liquid-containing silica was prepared by a molding machine.

Example 4: Evaluation of Effect of Treating Abomasal Displacement

Figure 3:
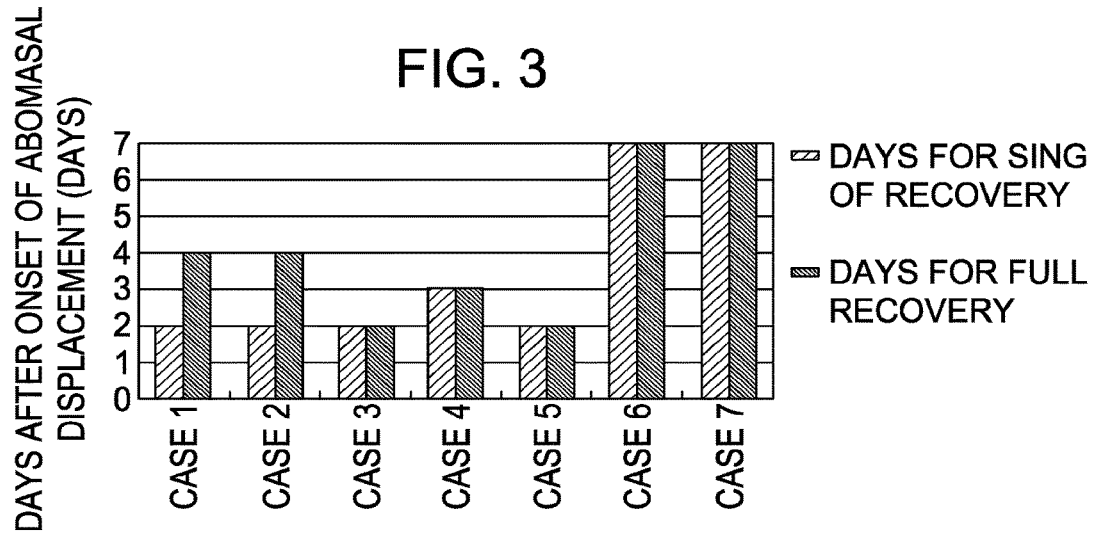
FIG. 3 is a graph showing a therapeutic effect of CNSL on abomasal displacement.

Adult female Holstein cattle were used in this test. Three tablets of Production Example 2 were fed per day (21.5 g in terms of CNSL) during a period from the onset to cure of abomasal displacement. This test was conducted for seven cases. The onset and cure of abomasal displacement were diagnosed and evaluated by a veterinarian. FIG. 3 shows the test results.

Tables 4 to 9 show the findings for the respective cases by the veterinarian. It should be noted that the abdominal distention was evaluated on a four-point scale: 1: very distended; 2: distended; 3: slightly distended; and 4: normal. The auscultation sound was evaluated on a four-point scale: 1: metallic sound; 2: splashing sound; 3: gargling sound; and 4: normal sound. The appetite, milk yield, and vitality were evaluated on a five-point scale: 1: very bad; 2: bad; 3: normal; 4: good; and 5: very good. The fecal condition was evaluated on a five-point scale: 1: bloody feces; 2: watery feces; 3: mud-like feces; 4: loose feces; and 5: normal feces.

TABLE 4

(Case 1)

Daily observation list

| Date | CNSL feeding | Abdominal distention | Auscultation sound | Appetite | Milk yield | Vitality | Fecal condition | Remark |
|---|---|---|---|---|---|---|---|---|
| Day 1: December 20 | ● | 3 | 2 | 2 | 2 | 2 | 2 | Hypophagia, diagnosed as abomasal displacement, medical treatment |
| Day 2: December 21 | ● | 3 | 2 | 3 | 3 | 2 | 2 | Medical treatment |
| Day 3: December 22 | ● | 3 | 2 | 4 | 4 | 3 | 3 | Scheduled for surgery, medical treatment |
| Day 4: December 23 | | 4 | 4 | 4 | 5 | 5 | 5 | Cured without surgery Recovery of appetite and milk yield Date of calving: December 15-onset on Day 5 after calving |

TABLE 5

(Cases 2 and 3)

Daily observation list

| Date | CNSL feeding | Abdominal distention | Auscultation sound | Appetite | Milk yield | Vitality | Fecal condition | Remark |
|---|---|---|---|---|---|---|---|---|
| Day 1: December 22 | ● | 2 | 2 | 2 | 3 | 2 | 2 | |
| Day 2: December 23 | ● | 2 | 3 | 2 | 3 | 2 | 2 | |
| Day 3: December 24 | ● | 4 | 3 | 2 | 3 | 2 | 2 | |
| Day 4: December 25 (Recurrence) | | 4 | 4 | 2 | 3 | 2 | 2 | Cured without surgery |
| Day 1: January 5 | ● | 2 | 3 | 2 | 3 | 2 | 2 | Hypophagia again, distension with gas |
| Day 2: January 6 | | 4 | 4 | 4 | 3 | 5 | 4 | Returned to normal state<br>Date of calving: December 21-onset on Day 1 after calving |

TABLE 6

(Case 4)

Daily observation list

| Date | CNSL feeding | Abdominal distention | Auscultation sound | Appetite | Milk yield | Vitality | Fecal condition | Remark |
|---|---|---|---|---|---|---|---|---|
| Day 1: December 27 | ● | 3 | 3 | 2 | 2 | 2 | 2 | Medical treatment on suspicion of abomasal displacement |
| Day 2: December 28 | ● | 3 | 3 | 2 | 2 | 2 | 2 | Abomasal displacement, distension with gas, medical treatment |
| Day 3: December 29 | | 4 | 4 | 5 | 5 | 5 | 5 | Cured without surgery<br>Recovery of appetite and milk yield<br>Date of calving: December 24-onset on Day 3 after calving |

TABLE 7

(Case 5)

Daily observation list

| Date | CNSL feeding | Abdominal distention | Auscultation sound | Appetite | Milk yield | Vitality | Fecal condition | Remark |
|---|---|---|---|---|---|---|---|---|
| Day 1: January 8 | ● | 4 | 3 | 2 | 3 | 3 | 4 | Hypophagia, suspected to have abomasal displacement |
| Day 2: January 9 | | 4 | 4 | 5 | 5 | 5 | 5 | Cured (Medical treatment)<br>Recovery of appetite<br>Date of calving: January 3-onset on Day 5 after calving |

TABLE 8

(Case 6)

Daily observation list

| Date | CNSL feeding | Abdominal distention | Auscultation sound | Appetite | Milk yield | Vitality | Fecal condition | Remark |
|---|---|---|---|---|---|---|---|---|
| Day 1: December 31 | ● | 2 | 3 | 2 | 2 | 2 | 3 | Medical treatment on suspicion of abomasal displacement |
| Day 2: January 1 | ● | 2 | 3 | 2 | 2 | 2 | 3 | Medical treatment on suspicion of abomasal displacement |

TABLE 8-continued (Case 6)

Daily observation list

| Date | CNSL feeding | Abdominal distention | Auscultation sound | Appetite | Milk yield | Vitality | Fecal condition | Remark |
|---|---|---|---|---|---|---|---|---|
| Day 3: January 2 | ● | 2 | 3 | 2 | 2 | 2 | 3 | Medical treatment on suspicion of abomasal displacement |
| Day 4: January 3 | ● | 2 | 3 | 2 | 2 | 2 | 2 | Medical treatment on suspicion of abomasal displacement |
| Day 5: January 4 | | 2 | 1 | 2 | 2 2 | 2 | 2 | Abdominal surgery (because of deteriorating abomasal displacement and distension with gas) |
| Day 14 | | 4 | 4 | 4 | 5 | 4 | 5 | Recovery of appetite Date of calving: December 29-onset on Day 2 after calving |

TABLE 9

(Case 7)

Daily observation list

| Date | CNSL feeding | Abdominal distention | Auscultation sound | Appetite | Milk yield | Vitality | Fecal condition | Remark |
|---|---|---|---|---|---|---|---|---|
| Day 1: January 13 | ● | 3 | 3 | 2 | 2 | 2 | 4 | Hypophagia, diagnosed as abomasal displacement, medical treatment |
| Day 2: January 14 | ● | 3 | 3 | 2 | 2 | 2 | 3 | Hypophagia, diagnosed as abomasal displacement, medical treatment |
| Day 3: January 15 | ● | 1 | 2 | 2 | 2 | 2 | 3 | Hypophagia, diagnosed as abomasal displacement, medical treatment |
| Day 4: January 16 | | 1 | 1 | 2 | 2 | 2 | 2 | Abdominal surgery |
| Day 5: January 17 | | 4 | 4 | 2 | 3 | 4 | 4 | Date of calving: Dec 29-onset on Day 2 after calving |

In five of seven cases, abomasal displacement was cured. Further, indications of the recovery, such as the improvement of appetite, increase in the milk yield, and amelioration of the fecal condition, were observed on Days 2 to 3, and abomasal displacement was completely cured on Days 2 to 4. The CNSL was found to have an effect of treating abomasal displacement.

Example 5: Evaluation of Effect of Improving Milk Yield Under Heat Stress

This test was conducted at two ranches in the same dairy cooperative region in a period (June 6 to September 21) when heat stress was applied. In ranch O, the feed to be fed was designed so as to have a forage/concentrate ratio of 44:56 and so that the dry matter intake was 20.1 to 22.8 kg per head. Before feeding of the cashew nut shell liquid-containing pellet, the milk yield and milk components were measured. The milk yield was calculated by dividing the amount of the whole milk gathered at the test ranch by the number of milk cows, and the milk component levels were analyzed for a sample obtained from the whole ilk. Further, the milk yield was corrected with a milk fat content, and the milk yield in terms of a milk fat content of 3.5% was defined as a 3.5 FCM value. A calculation equation is shown below.

3.5 FCM=0.432×Actual milk yield+16.23×(Actual milk yield×Actual milk fat percentage)

The heat stress is generally evaluated by temperature-humidity index (THI), and in the case of cattle, the index is defined as follows: 72 or less: comfortable, 73 to 80: slightly hot, 80 to 90: hot, 90 to 98: severely hot, and 98 or more: dangerous. If the THI value exceeds 73, the cattle feel stressed, resulting in decrease of the milk yield and milk quality. The milk yield may decrease by 10 to 20%. In this test, the heat stress was evaluated based on the THI value. The calculation equation is shown below. It should be noted that T represents a temperature (° C.), and H represents a relative humidity (%).

$$THI=0.8T+0.01H(T-14.3)+46.3$$

This test was conducted in a switchback system. More specifically, the feeding of the cashew nut liquid-containing pellet described in Production Example 1 was started in an amount of 50 g per day (5 g per day in terms of cashew nut shell liquid) per head. In test (1), the feeding was conducted for 20 days (feeding period) and stopped for 21 days (non-feeding period). In test (2), feeding for 21 days and non-feeding for 21 days were repeated again. The measurement of the milk yield and analysis of the milk quality were conducted before the feeding and at the final day of the respective test periods.

Figure 4:
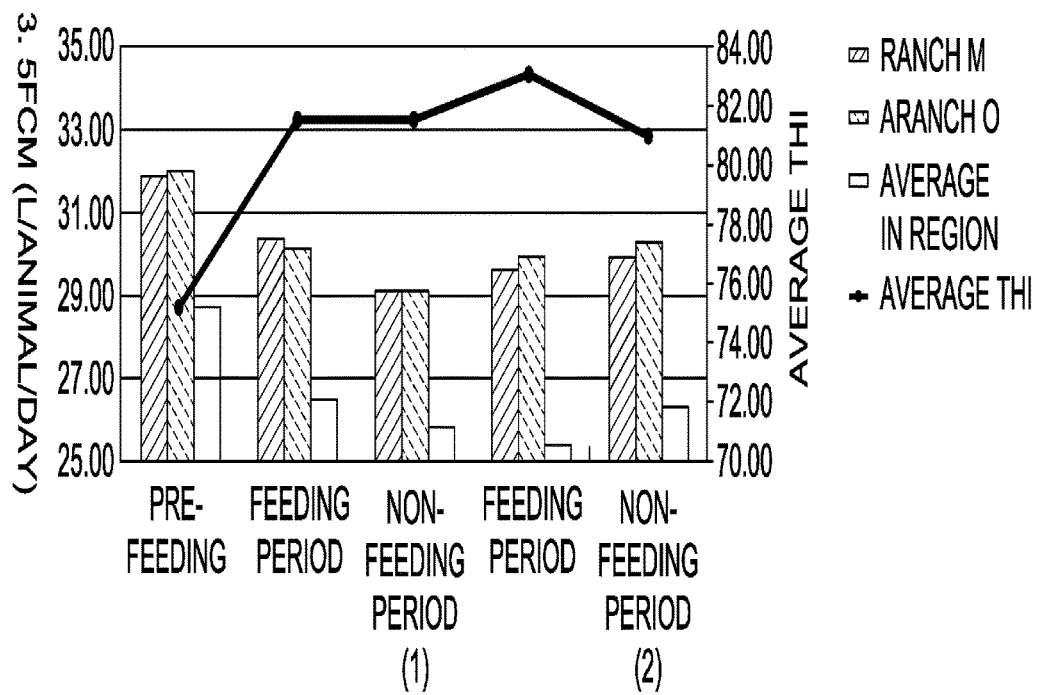
FIG. 4 is a graph showing changes in 3.5 FCM caused by feeding of CNSL and heat stress indices determined in the same period in ranches O and M.

In ranch M, the feed to be fed was designed so as to have a forage/concentrate ratio of 45:55 and so that the dry matter intake was 22.0 to 22.46 kg per day. Under the same test conditions as those in ranch O, the feeding of the cashew nut shell liquid-containing pellet and measurement of the milk yield and milk components were conducted. Tables 10 and 11 and FIG. 4 show the results.

It should be noted that milk fat content, solids-not-content, and milk protein content were measured in accordance with a measurement method described in:
"Ministerial Ordinance Concerning Compositional Standards, etc. for Milk and Milk Products"
(MHW Ordinance No. 52 dated Dec. 27, 1951)
Final revision: MHLW Ordinance No. 132 dated Oct. 30, 2007) Appendix
2. Compositional standards for Milk etc., and standards of production, cooking, and preservation methods
(7) Test method for compositional standards for milk etc.

feeding of the cashew nut shell liquid containing pellet, the milk yield and milk components were measured. The milk yield was calculated by dividing the amount of the whole milk gathered at the test ranch by the number of milk cows, and the milk component levels were analyzed for a sample obtained from the whole milk. 3.5 FCM and THI values were calculated in the same method as in Example 5.

This test was conducted by a switchback system. In test (1), the cashew nut shell liquid-containing pellet described in Production Example 1 was fed in an amount of 100 g per day (10 g per day in terms of cashew nut shell liquid) per

TABLE 10

Effect of feeding of CNSL on milk yield and milk quality (ranches M and O)

|  |  | Before feeding | Test (1) Feeding period | Test (1) Non-feeding period | Test (2) Feeding period | Test (2) Non-feeding period |
|---|---|---|---|---|---|---|
| Average THI |  | 75.16 | 81.42 | 81.35 | 82.72 | 80.85 |
| Ranch M | Milk yield (L/head) | 29.60 | 29.20 | 28.30 | 28.60 | 28.10 |
|  | 3.5 FCM (L/head) | 31.91 | 30.41 | 29.08 | 29.67 | 29.99 |
|  | Milk fat content (%) | 3.98 | 3.76 | 3.67 | 3.73 | 3.92 |
|  | Solids-not-fat content (%) | 8.80 | 8.61 | 8.53 | 8.44 | 8.53 |
|  | Milk protein content (%) | 3.25 | 3.15 | 3.09 | 3.00 | 3.10 |
| Ranch O | Milk yield (L/head) | 29.80 | 28.90 | 28.30 | 29.30 | 29.50 |
|  | 3.5 FCM (L/head) | 31.98 | 30.12 | 29.08 | 29.92 | 30.27 |
|  | Milk fat content (%) | 3.95 | 3.76 | 3.67 | 3.63 | 3.66 |
|  | Solids-not-fat content (%) | 8.81 | 8.69 | 8.73 | 8.66 | 8.64 |
|  | Milk protein content (%) | 3.24 | 3.16 | 3.18 | 3.15 | 3.14 |
| Average in region | Milk yield (L/head) | 27.90 | 25.50 | 24.95 | 24.40 | 25.20 |
|  | 3.5 FCM (L/head) | 28.72 | 26.41 | 25.76 | 25.37 | 26.35 |
|  | Milk fat content (%) | 3.68 | 3.72 | 3.70 | 3.75 | 3.78 |
|  | Solids-not-fat content (%) | 8.72 | 8.52 | 8.56 | 8.54 | 8.55 |
|  | Milk protein content (%) | 3.20 | 3.08 | 3.11 | 3.11 | 3.14 |

TABLE 11

Variation (%) of 3.5 FCM before and after feeding (ranches M and O)

|  | Before feeding | Test (1) Feeding period | Test (1) Non-feeding period | Test (2) Feeding period | Test (2) Non-feeding period |
|---|---|---|---|---|---|
| Average THI | 75.16 | 81.42 | 81.35 | 82.72 | 80.85 |
| Ranch M | 0.00 | −4.69 | −8.85 | −7.02 | −6.00 |
| Ranch O | 0.00 | −5.81 | −9.06 | −6.44 | −5.35 |
| Average in region | 0.00 | −8.03 | −10.29 | −11.65 | −8.25 |

The feeding of the cashew nut shell liquid-containing pellet was found to provide an effect of reducing decrease of the milk yield even under heat stress in both ranches. In addition, a comparison between the non-feeding period in test. (1) and the feeding period in test (2), which were under similar heat stress conditions, showed that increased milk yield and stable milk quality were achieved in the ranches where the cashew nut shell liquid-containing pellet was fed although the milk yield of the average in the region was lowered.

Example 6: Evaluation of Effect of Improving Milk Yield Under Heat Stress

Figure 5:
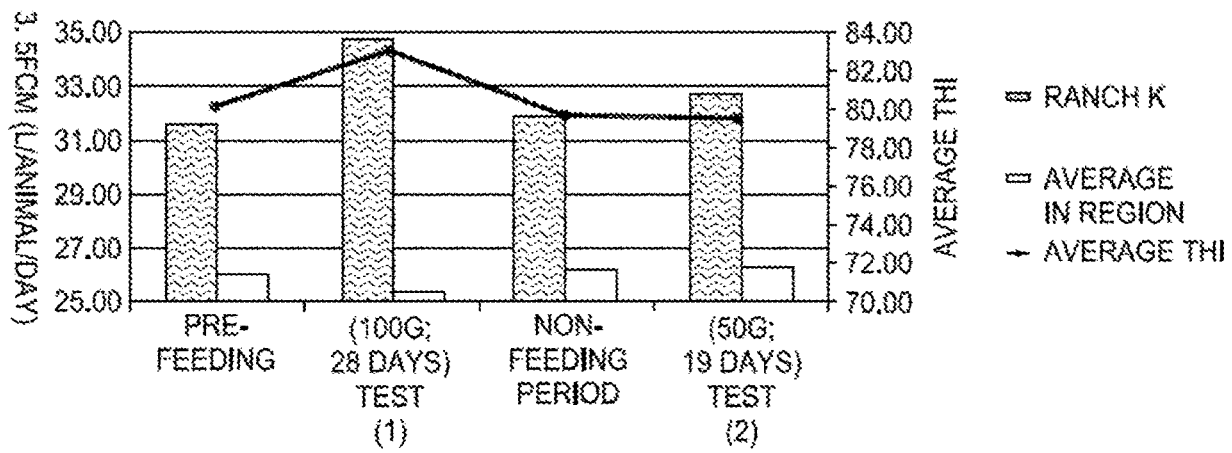
FIG. 5 is a graph showing changes in 3.5 FCM caused by feeding of CNSL and heat stress indices determined in the same period in ranch K.

This test was conducted at ranch K in the same dairy cooperative region as in Example 5 from July 21 to September 27. In ranch K, the feed to be fed was designed so as to have a forage/concentrate ratio of 43:57 and so that the dry matter intake was 22.2 to 23.64 kg per day. Before head. The feeding was conducted for 28 days and stopped for 6 days. In test (2), the cashew nut shell liquid-containing pellet was fed in an amount of 50 g per day (5 g per day in terms of cashew nut shell liquid) per head, and the test was completed after the pellet was fed for 19 days. The measurement of the milk yield and analysis of the milk quality were conducted before the feeding and at the final day of the respective test periods. Tables 12 and 13 and FIG. 5 show the results.

It should be noted that the milk fat content, solids-not-fat content, and milk protein content were measured in accordance with a measurement method described in:
"Ministerial Ordinance Concerning Compositional Standards, etc. for Milk and Milk Products"
(MHW Ordinance No. 52 dated Dec. 27, 1951)
Final revision: MHLW Ordinance No. 132 dated Oct. 30, 2007) Appendix
2. Compositional standards for milk etc., and standards of production, cooking, and preservation methods
(7) Test method for compositional standards for milk etc.

TABLE 12

Effect of feeding of CNSL on milk yield and milk quality (ranch K)

|  |  | Before feeding | Test (1) (100 g; 28 days) | Non-feeding period | Test (2) (50 g; 19 days) |
|---|---|---|---|---|---|
| Average THI |  | 80.14 | 83.02 | 79.70 | 79.55 |
| Ranch K | Milk yield (L/head) | 31.00 | 34.10 | 31.70 | 32.20 |

TABLE 12-continued

Effect of feeding of CNSL on milk yield and milk quality (ranch K)

| | | Before feeding | Test (1) (100 g; 28 days) | Non-feeding period | Test (2) (50 g; 19 days) |
|---|---|---|---|---|---|
| | 3.5 FCM (L/head) | 31.61 | 34.77 | 31.96 | 32.78 |
| | Milk fat content (%) | 3.62 | 3.62 | 3.55 | 3.61 |
| | Solids-not-fat content (%) | 8.65 | 8.60 | 8.63 | 8.58 |
| | Milk protein content (%) | 3.09 | 3.07 | 3.09 | 3.06 |
| Average in region | Milk yield (L/head) | 25.50 | 24.40 | 25.20 | 25.20 |
| | 3.5 FCM (L/head) | 26.00 | 25.39 | 26.26 | 26.31 |
| | Milk fat content (%) | 3.62 | 3.75 | 3.76 | 3.77 |
| | Solids-not-fat content (%) | 8.57 | 8.54 | 8.55 | 8.55 |
| | Milk protein content (%) | 3.09 | 3.10 | 3.14 | 3.14 |

TABLE 13

Variation (%) of 3.5 FCM before and after feeding (%) (ranch K)

| | Before feeding | Test (1) (100 g; 28 days) | Non-feeding period | Test (2) (50 g; 19 days) |
|---|---|---|---|---|
| Average THI | 75.16 | 81.42 | 81.35 | 82.72 |
| Ranch K | 0.00 | 10.00 | 1.12 | 3.71 |
| Average in region | 0.00 | −2.33 | 1.03 | 1.18 |

In ranch K, the feeding of the cashew nut shell liquid-containing pellet was found to provide an effect of reducing decrease of the milk yield even under heat stress. In particular, in test (1), although the heat stress rapidly increased to significantly lower the average milk yield in the region, a significant increase in the milk yield and stable milk quality were achieved in ranch K. In test (2), the milk yield in ranch K was found to significantly increase compared with the average milk yield in the region.

Example 7: Evaluation of Effect of Improving Milk Quality

This test was conducted in a ranch where the average number of milk cows was 50 per day, and adult female Holstein cattle were used in this test. The feed was fed by separate feeding, and the forage/concentrate ratio was finely adjusted depending on the condition in the range of 0.45 to 0.60. The feed was designed so that the dry matter intake was 23 to 25 kg per day.

Before the feeding of the cashew nut shell liquid-containing pellet, the milk yield and milk components were measured. The milk yield was calculated by dividing the amount of the whole milk gathered at the test ranch by the number of milk cows, and the milk component levels were analyzed for a sample obtained from the whole milk. The milk yield and milk quality for 11 days before the feeding of the cashew nut shell liquid-containing pellet were calculated as control values. After that, the cashew nut shell liquid-containing pellet described in Production Example 1 was fed for 21 days in an amount of 50 g per day (5 g per day in terms of cashew nut shell liquid) per head, and changes in the milk yield and milk quality were observed.

The milk fat content, solids-not-fat content, and milk protein content were measured in accordance with a measurement method described in:

"Ministerial Ordinance Concerning Compositional Standards, etc. for Milk and Milk Products"
(MHW Ordinance No. 52 dated Dec. 27, 1951)
Final revision: MHLW Ordinance No. 132 dated Oct. 30, 2007) Appendix
2. Compositional standards for milk etc., and standards of production, cooking, and preservation methods
(7) Test method for compositional standards for milk etc.
Table 14 shows the test results.

TABLE 14

Effect of feeding of CNSL on milk yield and milk quality

| | Before feeding | Feeding period | Variation |
|---|---|---|---|
| Average THI | 82.82 | 81.99 | −0.83 |
| Milk yield (L/head) | 30.20 | 29.60 | −0.60 |
| 3.5 FCM (L/head) | 30.94 | 30.47 | −0.47 |
| Milk fat content (%) | 3.65 | 3.68 | 0.03 |
| Solids-not-fat content (%) | 8.27 | 8.39 | 0.12 |
| Milk protein content (%) | 2.88 | 3.15 | 0.27 |
| Milk urea nitrogen (mg/dL) | 13.10 | 11.50 | −1.60 |

In the case where the cashew nut shell liquid-containing pellet was fed, the milk yield was not significantly lowered even under heat stress, and the milk quality was more improved in all the items. In particular, the solids-not-fat content and milk protein content were significantly improved, while the milk urea nitrogen (MUN) was reduced. This is probably because, as mentioned above, the milk protein content was increased through efficient conversion of nitrogen into a milk protein in a body, resulting in reduction of MON which is free nitrogen.

In general, an excessive amount of MUN is considered to cause not only decrease of milk quality such as a milk protein and lactose but also decrease of the reproductive performance such as prolongation in non-pregnant period and increase of the number of artificial inseminations. Therefore, in milk cows which are industrial animals, the improvement of the milk yield and milk quality and prevention of decrease of the reproductivity are very important, and the cashew nut shell liquid-containing pellet which can exert its effect on both the improvement and prevention even under heat stress is considered to be industrially significant.

Production Example 3

220 kg of cashew nut shells were obtained from Cashew Trading Co., Ltd., and the shells were compressed, thereby producing 67 kg of cashew nut shell liquid. In Techno Paudalton Co., Ltd., Cellulose, silicic anhydride, maltose, citric anhydride, and sodium dihydrogenphosphate were mixed with the cashew nut shell liquid, thereby preparing a cashew nut shell liquid-containing tablet. Further, in order to improve the usability, the tablet was covered with oblate (starch).

Example 8: Evaluation of Effect of Treating Abomasal Displacement

Figure 6:
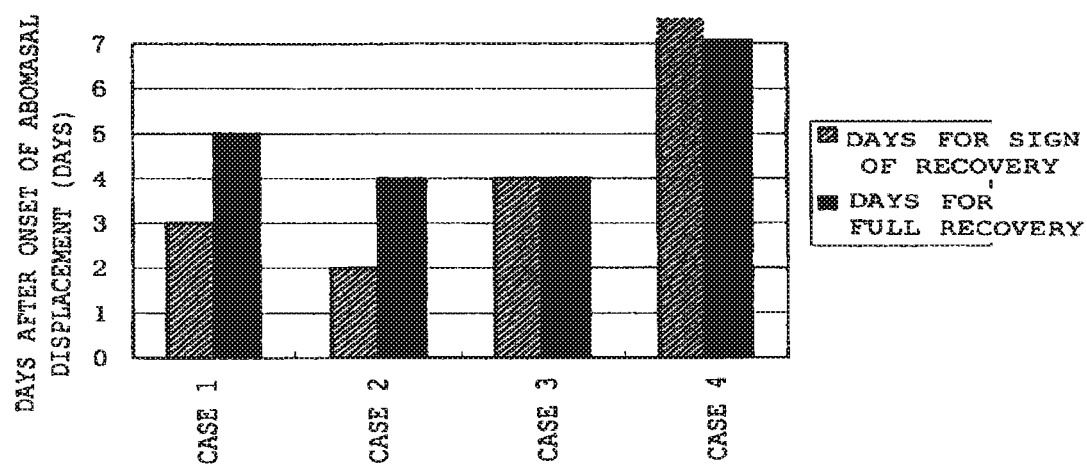
FIG. 6 is a graph showing a therapeutic effect of CNSL on abomasal displacement.
Figure 4:
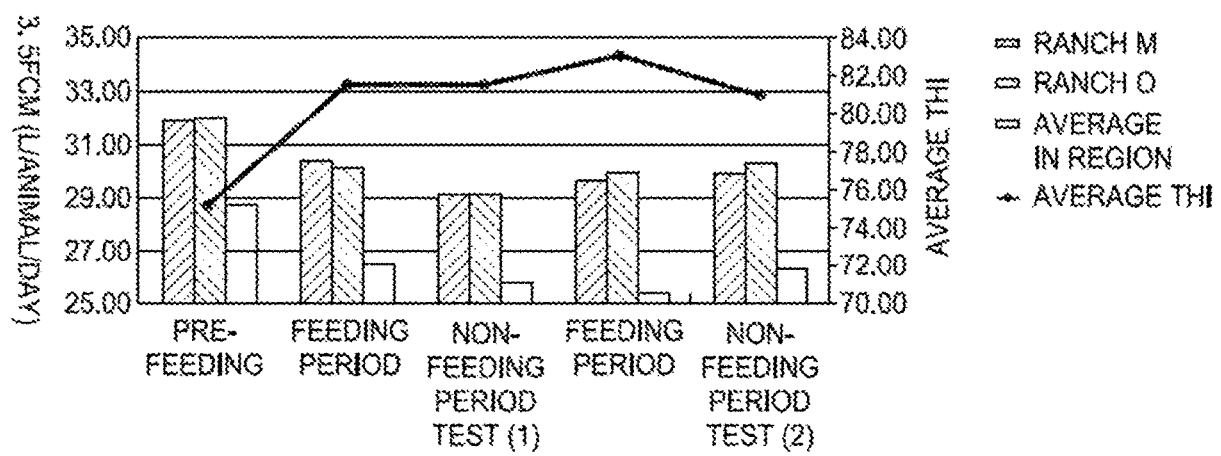

Adult female Holstein cattle were used in this test. Sixteen tablets of Production Example 3 were fed per day (10 g in terms of CNSL) during a period from the onset to cure of abomasal displacement. This test was conducted for four cases. Tables 0.15 to 18 and FIG. 6 show the results. The onset and cure of abomasal displacement were evaluated based on diagnosed and evaluated by a veterinarian.

Tables 15 show the findings for the respective cases by the veterinarian. It should be noted that the abdominal distention was evaluated on a four-point scale: 1 very distended; 2: distended; 3: slightly distended; and 4: normal. The auscultation sound was evaluated on a four-point scale: 1: metallic sound; 2: splashing sound; 3: gargling sound; and 4: normal sound. The appetite, milk yield, and vitality were evaluated on a five-paint scale: 1: very bad; 2: bad; 3: normal; 4: good; and 5: very good. The fecal condition was evaluated on a five-point scale: 1: bloody feces; 2: watery feces; 3: mud-like feces; 4: loose feces; and 5: normal feces.

TABLE 15

(Case 1)

Daily observation list

| Date | CNSL feeding | Abdominal distention | Auscultation sound | Appetite | Milk yield | Vitality | Fecal condition | Remark |
| --- | --- | --- | --- | --- | --- | --- | --- | --- |
| Day 1: August 14 | ● | 2 | 1 | 1 | 2 | 2 | 5 | Took only hay, ping sound on the right side |
| Day 2: August 15 | ● | 2 | 1 | 1 | 2 | 2 | 5 | Hypophagia, right ping sound or tympanic resonance |
| Day 3: August 16 | ● | 2 | 1 | 3 | 2 | 2 | 5 | Improved appetite, right ping sound |
| Day 4: August 17 | | 4 | 4 | 4 | 3 | 3 | 5 | Recovery of appetite, recovery of abdominal distension with gas |
| Day 5: August 18 | | 4 | 4 | 4 | 4 | 4 | 5 | Recovery of appetite Date of calving: August 11-onset on Day 4 after calving |

TABLE 16

(Case 2)

Daily observation list

| Date | CNSL feeding | Abdominal distention | Auscultation sound | Appetite | Milk yield | Vitality | Fecal condition | Remark |
| --- | --- | --- | --- | --- | --- | --- | --- | --- |
| Day 1: August 28 | ● | 2 | 1 | 3 | 3 | 2 | 5 | Metallic sound on the right side |
| Day 2: August 29 | ● | 4 | 4 | 4 | 2 | 4 | 5 | Recovery of abdominal distension with gas, appetite, and vitality |
| Day 3: August 30 | ● | 4 | 4 | 4 | 2 | 4 | 5 | |
| Day 4: August 31 | | 4 | 4 | 4 | 3 | 4 | 5 | Returned to normal state Date of calving: August 26-onset on Day 3 after calving |

TABLE 17

(Case 3)

Daily observation list

| Date | CNSL feeding | Abdominal distention | Auscultation sound | Appetite | Milk yield | Vitality | Fecal condition | Remark |
| --- | --- | --- | --- | --- | --- | --- | --- | --- |
| Day 1: September 9 | ● | 2 | 1 | 1 | 2 | 2 | 2 | Took only hay, tympanic resonance on the right side |
| Day 2: September 10 | ● | 2 | 1 | 1 | 3 | 2 | 5 | Metallic sound on the right side |
| Day 3: September 11 | ● | 4 | 4 | 1 | 3 | 3 | 5 | Took only hay, recovery of abdominal distension with gas |
| Day 4: September 12 | | 4 | 4 | 4 | 3 | 4 | 5 | Recovery of appetite, returned to normal state Date of calving: September 6-onset on Day 4 after calving |

TABLE 18

(Case 4)

Daily observation list

| Date | CNSL feeding | Abdominal distention | Auscultation sound | Appetite | Milk yield | Vitality | Fecal condition | Remark |
|---|---|---|---|---|---|---|---|---|
| Day 1: September 5 | ● | 2 | 1 | 2 | 2 | 2 | 3 | Poor appetite, metallic sound on the left side |
| Day 2: September 6 | ● | 2 | 1 | 1 | 2 | 2 | 3 | Metallic sound on the right side, took only hay |
| Day 3: September 7 | ● | 2 | 1 | 1 | 1 | 2 | 3 | Matallic sound on the right side, took only hay Date of calving: August 23-onset on Day 13 after calving twin calving, retention of placenta, persistent diarrhea before feeding |

In three of four cases, abomasal displacement was cured. Further, indications of the recovery, such as the improvement of appetite, increase in the milk yield, and amelioration of the fecal condition, were observed on Days 2 to 3, and abomasal displacement was completely cured at Days 2 to 4 From the results, the CNSL was found to have an effect of treating abomasal displacement. Further, the effect of treating abomasal displacement was obtained by feeding a smaller amount of CNSL than that in Example 4.

In this test, the cashew nut shell liquid-containing tablet was fed after the onset of abomasal displacement, and the effect of the tablet was examined. Generally, in many cases, perinatal diseases develop after calving due to the feeding system particularly in the dry period. However, the perinatal disease may be controlled comprehensively by feeding the tablet in the dry period because preventive feeding of the tablet before the onset of the perinatal diseases was effective in Example 3.

Example 9: Evaluation of Effect of Improving Reproductivity

Adult female Holstein cattle were used in this test. Individuals which had calved were divided at random into test group and control group, and the agent of Production Example 1 was fed to the individuals in test group for 5 days from the date of calving in an amount of 100 g (10 g in terms of CNSL) per day. It should be noted that primiparous cows were not included in the data for statistics because the cows were managed in a different way before and after calving. 9 cow (two calvings: 2 cows, three calvings: 4 cows, four calvings: 1 cow, five calvings: 1 cow, six calvings: 1 cow) were allocated test group (fed with CNSL) and 5 cows (three calvings: 5 cows) were allocated to control group (fed with no CNSL). Although the feed to be fed was modified depending on the condition of the cows, the feed was designed so that 7 kg of timothy and 2 to 3 kg of a concentrate feed were fed on average per day.

The reproductivity was evaluated based on general indices, more specifically, the number of artificial insemination, the days of non-pregnant, actual days of non-pregnant, days to first service, a pregnancy rate at first service, a pregnancy rate, and an detection rate of estrus. As for days of non-pregnant, the percentages of individuals with non-pregnant days of 90 days or less (evaluated as good) and individuals with non-pregnant days of 120 days or more (evaluated as not good) were also calculated. Table 19 shows the test results.

TABLE 19

Effect of feeding of CNSL on reproductivity

| | CNSL group | Control group | Variation |
|---|---|---|---|
| n | 9 | 5 | — |
| Number of insemination (times) | 2.0 | 2.6 | −0.6 |
| Days of non-pregnant | 111 | 137 | −26.0 |
| 90 days or less (%) | 33.3 | 20.0 | 13.3 |
| 120 days or more (%) | 33.3 | 60.0 | −26.7 |
| Days of first insemination | 78.9 | 78.7 | 0.2 |
| Pregnancy rate at first service (%) | 33.3 | 16.7 | 16.6 |
| Pregnancy rate (%) | 50.0 | 38.5 | 11.5 |
| Actual days of non-pregnant | 32.1 | 58.3 | −26.2 |
| Detection rate of estrus (%) | 79.10 | 68.85 | 10.2 |

Number of insemination=times of artificial insemination

Days of non-pregnant=last conception day−last calving day

Days of first insemination=first insemination day−last calving day

Pregnancy rate at first service=rate of conception achieved by first insemination Pregnancy rate=number of individuals with conception (group total)/total times of artificial insemination×100

Actual days of non-pregnant=days from first to last insemination

First insemination day=first artificial insemination day after calving

Last insemination day=latest day of artificial insemination

Detection rate of estrus (whole group)=average number of insemination/((average actual days of non-pregnant/21)+1×100

The feeding of the cashew nut shell liquid-containing pellet was found to provide better results in almost all the items compared with control group. In particular, significant effects of reducing the number of insemination, decreasing days of non-pregnant, improving the pregnancy rate, and decreasing actual days of non-pregnant were confirmed. Further, the feeding of CNSL was able to achieve the conception rate and the estrus detection rate at levels exceeding 50 to 60% and 70% or more of target levels, respectively. The results show that the feeding of the cashew nut shell liquid-containing pellet was found to significantly improve the reproductivity in each individual and to further significantly improve the reproductivity in the detection rate of estrus and pregnancy rate in each group.

INDUSTRIAL APPLICABILITY

According to the present invention, it is possible to improve the milk yield and milk quality of a ruminant and to prevent or treat a perinatal disease, and hence the present invention is useful in livestock field. Further, the present invention can improve the reproductive performance to efficiently produce

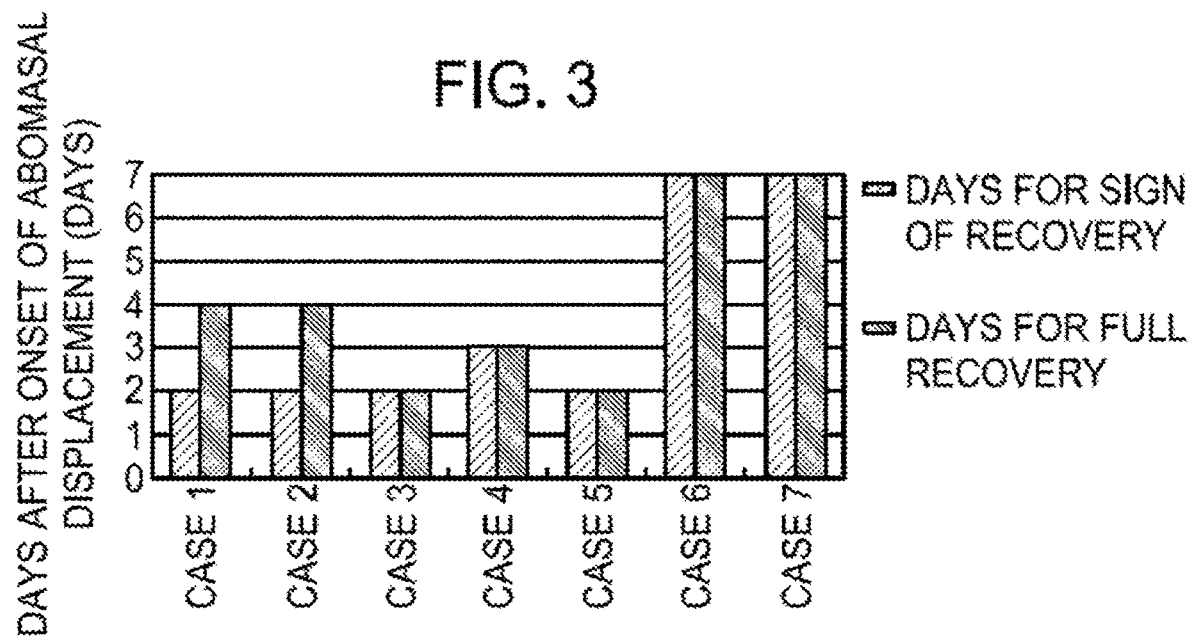

The invention claimed is:

1. A method of improving reproductivity of a ruminant in need thereof, comprising:
feeding the ruminant in need thereof a reproductivity-improving effective amount of at least one agent selected from the group consisting of a cashew nut shell liquid, and a heat-treated cashew nut shell liquid in an amount effective to improve the reproductivity of the ruminant.

2. The method of claim 1, wherein the agent is fed to the ruminant in an amount of 0.01 to 500 g per ruminant per day.

3. The method of claim 1, wherein the ruminant is selected from the group consisting of a cow, a goat and a sheep.

4. The method of claim 1, wherein the ruminant is a female Holstein cow.

5. The method of claim 1, wherein the agent is fed to the ruminant after a calving.

6. The method of claim 5, wherein the agent is fed to the ruminant in an amount of 1-100 g of cashew shell nut liquid per day.

7. The method of claim 6, wherein the agent is fed to the ruminant at least 5 days after the calving.

8. The method of claim 1, wherein improving the reproductivity of the ruminant includes at least one condition selected from the group consisting of improving the rate of estrus of the ruminant, reducing the actual days of non-pregnancy of the ruminant, increasing the pregnancy rate of the ruminant and increasing the pregnancy rate at first service of the ruminant.

9. The method of claim 1, wherein the agent comprises a cashew nut shell liquid containing 55 to 80 mass % of anacardic acid, 5 to 20 mass % of cardanol, and 5 to 30 mass % of cardol.

10. The method of claim 1, wherein the agent comprises a cashew nut shell liquid containing 0 to 10 mass % of anacardic acid, 55 to 80 mass % of cardanol, and 5 to 30 mass % of cardol.

11. The method of claim 1, wherein the cashew nut shell liquid and/or the heat-treated cashew nut shell liquid is administered to the ruminant in an amount of 10 g or less per ruminant per day.

12. The method of claim 1, comprising administering the cashew nut shell liquid and/or the heat-treated cashew nut shell liquid to the ruminant together with at least one oil absorbent selected from the group consisting of magnesium oxide, stearate, talc, zeolite, diatom earth and silica in a mass ratio of 100:20 to 100:180.

13. The method of claim 1, wherein the ruminant is raised with a feed having a ratio by weight of a forage to a total weight of the forage and a concentrate feed of from 0.3 to 1.0.

* * * * *

UNITED STATES PATENT AND TRADEMARK OFFICE
CERTIFICATE OF CORRECTION

PATENT NO. : 9,694,041 B2
APPLICATION NO. : 14/962591
DATED : July 4, 2017
INVENTOR(S) : Koichi Kaneda et al.

It is certified that error appears in the above-identified patent and that said Letters Patent is hereby corrected as shown below:

Delete Sheet 2 of 5 in its entirety and replace Fig. 3 with Fig. 3 as shown on the attached sheet.

Delete Sheet 3 of 5 in its entirety and replace Fig. 4 with Fig. 4 as shown on the attached sheet.

Delete Sheet 4 of 5 in its entirety and replace Fig. 5 with Fig. 5 as shown on the attached sheet.

Signed and Sealed this
Tenth Day of April, 2018

Andrei Iancu
*Director of the United States Patent and Trademark Office*